United States Patent [19]

Feuerherd et al.

[11] Patent Number: 5,130,356

[45] Date of Patent: Jul. 14, 1992

[54] MOLDING FOR OPTICAL PURPOSES

[75] Inventors: Karl-Heinz Feuerherd, Hettenleidelheim; Carola Hedtmann-Rein, Hirschberg; Ludger Leber, Dannstadt-Schauernheim, all of Fed. Rep. of Germany

[73] Assignee: BASF Aktiengesellschaft, Ludwigshafen, Fed. Rep. of Germany

[21] Appl. No.: 473,453

[22] Filed: Feb. 1, 1990

[30] Foreign Application Priority Data

Feb. 1, 1989 [DE] Fed. Rep. of Germany ....... 3902939

[51] Int. Cl.⁵ ............................ C08K 5/08; C08K 5/13; C08K 5/357
[52] U.S. Cl. ............................... 524/96; 428/64; 524/156; 524/323; 524/348; 524/358; 525/132; 525/390; 525/905; 552/304; 558/37; 568/730
[58] Field of Search ................ 524/348, 358, 96, 323, 524/156; 525/390, 905, 132

[56] References Cited

U.S. PATENT DOCUMENTS

| | | | |
|---|---|---|---|
| 3,383,395 | 5/1968 | Schmukler et al. | 260/398.5 |
| 4,234,706 | 11/1980 | White | 525/390 |
| 4,373,065 | 2/1983 | Prest, Jr. | |
| 4,719,170 | 1/1988 | Schrott et al. | 430/270 |

FOREIGN PATENT DOCUMENTS

| | | |
|---|---|---|
| 0225801 | 6/1987 | European Pat. Off. . |
| 63-013722A | 7/1986 | Japan . |
| 63-056832A | 8/1986 | Japan . |
| 63-089335A | 10/1986 | Japan . |

OTHER PUBLICATIONS

Wanzlick, Lehmann–Horchler, Mohrmann, Gritzki, Heidepriem and Pankow, Neuere Methoden der Präparativen Organischen Chemie IV, Synthesen mit naszierenden Chinonen, Angew Chem. 76 (1964), 313–356.

*Primary Examiner*—Jacob Ziegler
*Attorney, Agent, or Firm*—Keil & Weinkauf

[57] ABSTRACT

A novel, optically transparent, isotropic molding for optical purposes which is free of orientation birefringence consists of a mixture of polyphenylene ethers, vinylaromatic polymers and additives. The novel molding contains traces of novel diphenoquinone and/or diphenohydroquinone derivatives as additives and may also contain novel ammonium salts of sulfuric acid half esters of diphenohydroquinones as further additives. The novel molding has a yellowness index (YI) of from 40 to 90. It can be produced in a simple manner by injection molding processes. The novel molding in the form of a circular disk having a central hole is very useful as a dimensionally stable substrate of audio compact disks (CD), audiovisual compact disks (CDV), laser-optical computer disks and magneto-optical computer disks, and data media of this type which contain these novel dimensionally stable substrates have particularly advantageous performance characteristics.

14 Claims, No Drawings

MOLDING FOR OPTICAL PURPOSES

The present invention relates to an optically transparent, isotropic molding for optical purposes which is free of orientation birefringence and consists of a novel mixture of polyphenylene ethers, vinylaromatic polymers and additives.

Optically transparent, isotropic moldings for optical purposes which are free of orientation birefringence and consist of a mixture of polyphenylene ethers and vinylaromatic polymers are known from the prior art. For example, US-A-4 373 065 describes a laser-optical computer disk which contains at least one layer of a mixture of poly-(2,6-dimethylphen-l,4-ylene ether) and polystyrene. This mixture, which is free of orientation birefringence, consists of from 36 to 40% by weight of poly-(2,6-dimethylphen-l,4-ylene ether) and from 60 to 64% by weight of polystyrene, the mixing ratio used in each case being dependent on the mean molecular weight of the polystyrene To compensate the orientation birefringence of the polystyrene, about 38-40% by weight of poly-(2,6-dimethylphen-1,4-ylene ether) are required for polystyrene having a mean molecular weight of about $6.7 \times 10^5$, about 36-40% by weight for polystyrene having a mean molecular weight of from $10^5$ to $3 \times 10^5$, about 37-39% by weight for polystyrene having a number average molecular weight of from $10^5$ to $1.1 \times 10^5$ and about 31-33% by weight for polystyrene having a mean molecular weight of $10^4$. Instead of this phenylene ether, it is also possible to use the 2,6-diethyl-, 2-methyl-6-ethyl-, 2-methyl-6propyl, 2,6-dipropyl- or 2-ethyl-6-prop-vl-substituted polyphenylene ether. Instead of polystyrene, poly-(amethylstyrene) or copolymers of p-chlorostyrene and o-chlorostyrene are also suitable.

EP-A 0 225 801 discloses a molding for optical purposes which essentially consists of vinylaromatic polymers and polyphenylene ethers, the latter having an intrinsic viscosity $[\eta]$ of from 0.3 to 0.7, measured in chloroform at 25° C. In order to produce mixtures which are free of orientation birefringence, from 30 to 70, preferably from 40 to 55, % by weight of the vinylaromatic polymer are mixed with from 70 to 30, in particular from 60 to 45, % by weight of polyphenylene ethers. The optically transparent, isotropic mixtures prepared in this manner and free of orientation birefringence can be converted into moldings for optical purposes, in particular into dimensionally stable substrates of laser-optical computer disks, by injection molding processes.

Furthermore, JP-A-63-089335 discloses a process for the production of an optically transparent, isotropic molding for optical purposes which is free of orientation birefringence, in which process organic phosphorus compounds and/or sterically hindered phenols are added as stabilizers to the mixture of polyphenylene ethers and vinylaromatic polymers to be processed. This reduces the internal stress and the orientation birefringence, suppresses decomposition during processing and improves the optical transmission.

JP-A-63-056832 discloses a magneto-optical computer disk whose substrate consists of a mixture of vinylaromatic polymers and polyphenylene ethers Suitable vinylaromatics for producing these polymers are styrene, m-methylstyrene, p-methylstyrene, o-chlorostyrene and p-chlorostyrene. The vinylaromatic polymers may also contain other monomers, such as methacrylonitrile, n-propyl methacrylate, n-butyl methacrylate, maleic anhydride or N-phenylmaleimide. These dimensionally stable substrates exhibit good adhesion to the protective layers present on top of them.

JP-A-63-013722 discloses an injection molding process for the production of a dimensionally stable substrate from vinylaromatic polymers and polyphenylene ethers. In this process, the mixture of vinylaromatic polymers and polphenylene ethers is injection molded at a melt temperature of from 300 to 340° C.

German Patent application P 37 27 093.1 which corresponds to U.S Pat. application Ser. No. 07/231,384, describes a laser-optical computer disk whose dimensionally stable substrate consists of an optically transparent, isotropic, homogeneous mixture of poly-(2,6-dimethylphen-l,4-ylene ether) and styrene polymers, the said mixture being free of orientation birefringence. The styrene polymers used here contain from 0.1 to 8% by weight of polymerized acrylonitrile, from 1 to 60% by weight of polymerized α-methylstyrene, from 1 to 60% by weight of polymerized p-methylstyrene and/or from 0.1 to 10% by weight of polymerized (meth)acrylates, the percentages being based on the styrene polymers. These additionally present monomer units may be randomly distributed in the polymer main chains of the polystyrene. However, they can also be present in the form of pure oligomeric or polymeric blocks which are either incorporated in the polymer main chains of the polystyrene and/or bonded as side radicals to these polymer main chains. Furthermore, the additional monomer units may form oligomeric or polymeric homo- or copolymers or block or graft copolymers, which are prepared separately and then added to the polystyrene. Moreover, both the α-methylstyrene and the p-methylstyrene may form the monomer units of oligomeric random copolymers which are prepared separately and then added to the polystyrene. Regardless of the manner in which the styrene polymer has been modified, the mixture which is free of orientation birefringence contains not less than 40% by weight of polymerized styrene in every case. These mixtures can readily be processed by injection molding to give dimensionally stable substrates for laser-optical computer disks, and dimensionally stable substrates produced from these mixtures will have a good track shape, are very flat and have particularly low orientation birefringence.

In spite of the progress to date, the optically transparent, isotropic moldings for optical purposes which are free of orientation birefringence and consist of mixtures of polyphenylene ethers, vinylaromatic polymers and, if required, additives, in particular, however, the dimensionally stable substrates produced from these mixtures for laser-optical computer disks, still have disadvantages which necessitate continuous further development and improvement. For example, the conventional dimensionally stable substrates consisting of mixtures of vinylaromatic polymers and polyphenylene ethers often result in a signal-to-noise ratio which does not meet practical requirements. Moreover, specks or gel particles are frequently formed during the production of the dimensionally stable substrates by injection molding; in some cases, carbonized particles are even formed Furthermore, the laser-optical and magneto-optical computer disks which contain these known dimensionally stable substrates have a comparatively high bit error rate. In addition, in laser-optical computer disks which have amorphous, thermally alterable, dye-containing recording layers, UV radiation may result in destruction of the recording layer, which has an adverse effect on the signal-to-noise ratio and the bit error rate of the relevant laser-optical computer disks. Furthermore, it is still necessary for a dye to be mixed with the conventional dimensionally stable substrates for identification purposes, which always leads to processing problems and/or to problems of compatibility.

It is an object of the present invention to provide a novel, optically transparent, isotropic molding for optical purposes which is free of orientation birefringence and consists of a mixture of polyphenylene ethers, vinylaromatic polymers and additives and which no longer has the disadvantages of the prior art. This novel molding for optical purposes should be particularly suitable as a dimensionally stable substrate for audio compact disks (CD), for audiovisual compact disks (CDV), for laser-optical computer disks and for magneto-optical computer disks.

We have found that this object is achieved, surprisingly, by a novel, optically transparent, isotropic molding for optical purposes which is free of orientation birefringence and which consists of a mixture of polyphenylene ethers, vinylaromatic polymers and additives, wherein small amounts of novel diphenoquinone derivatives and/or diphenohydroquinone derivatives are used as additives.

The present invention accordingly relates to an optically transparent, isotropic molding for optical purposes which is free of orientation birefringence and consists of a mixture of polyphenylene ethers, vinylaromatic polymers and additives, wherein the mixture contains from 1 to 1,000 ppm, based on its total amount, of one or more additives of the general formula I

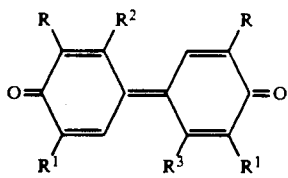

and/or of the general formula II

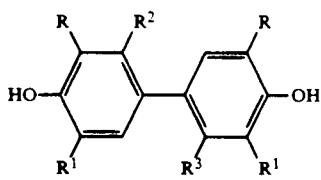

where R and $R^1$ may be identical or different and are each hydrogen, chlorine, bromine, substituted or unsubstituted $C_1-C_6$-alkyl, $C_3-C_6$-alkenyl, substituted or unsubstituted $C_5-C_{18}$-aryl or $C_1-C_6$-alkoxy, and a) the radicals R are each hydrogen or methyl if the radicals $R^1$ are each chlorine or bromine,
b) the radicals R are each methyl if the radicals $R^1$ are each isopropyl and
c) the tert-butyl group is excepted, and $R^2$ and $R^3$ are each hydrogen, hydroxyl or $N(R^4)_2$, and
d) $R^3$ is hydrogen only when $R^2$ is hydroxyl or $N(R^4)_2$,
e) $R^3$ is $N(R^4)_2$ only when $R^2$ has the same meaning, and
f) the two radicals $R^4$ on one nitrogen atom may be identical or different and are each branched, straight-chain or cyclic alkyl or branched, straight-chain or cyclic aza- or oxaalkyl, or the two radicals $R^4$ are bonded cyclically to one another via a divalent group.

We have also found novel derivatives of diphenoquinone and diphenohydroquinone which are very useful as additives for mixtures of vinylaromatic polymers and polyphenylene ethers.

The optically transparent, isotropic molding for optical purposes which is free of orientation birefringence and consists of a mixture of polyphenylene ethers, vinylaromatic polymers and additives is referred to below in brief as the novel molding.

The essential components of the novel moldings for the purposes of the present invention are the novel additives of the general formula I and/or II.

The novel moldings may contain one of these novel additives I or II. However, they may also contain a plurality of novel additives I or II. Furthermore, the novel moldings may contain a mixture of one or more novel additives I and one or more novel additives II.

The novel additives I and/or II are present in traces in the novel moldings, i.e. generally in an amount of from 1 to 1,000 ppm, based on the total amount of the mixture which forms the novel molding. It is of course possible for the novel additives I and/or II to be present in larger amounts in the novel moldings However, the novel additives I and/or II display their advantageous technical effect completely when present in an amount of only 1-1,000 ppm, so that there is in principle no need to increase the amount added.

Examples of suitable radicals R and $R^1$ in the general formulae I and II are hydrogen, chlorine, bromine, methyl, ethyl, propyl, isopropyl, n-butyl, sec-butyl, n-pentyl, n-hexyl, chloromethyl, 2-chloroethyl, 3-chloropropyl, prop-2-en-l-yl, but-3-en-l-yl, pent-4-en-1-yl, 3-methylbut-2-en-l-yl, hex-5-en-l-yl, phenyl, naphth-1-yl, naphth-2-yl, 2-methylphen-l-yl, 4-methylphen-l-yl, 2-phenylphen-l-yl, 3-phenylphen-l-yl, 4-tert-butylphen-l-yl, terphenylyl, methoxy, eth-1-yloxy, prop-1-yloxy, n-but-l-yloxy, n-pent-l-yloxy and n-hex-l-yloxy.

The radicals R and $R^1$ in the novel additives I and/or II may be identical or different, but the following two restrictions are applicable:

(a) if $R^1$ is chlorine or bromine, R is hydrogen or methyl and
(b) if $R^1$ is isopropyl, R is methyl; and
(c) R and $R^1$ are not tert-butyl.

Preferred radicals R and $R^1$ in the general formulae I and/or II are methyl and methoxy, of which methyl is very particularly preferred.

Examples of suitable radicals $R^2$ and $R^3$ in the general formulae I and II are hydrogen, hydroxyl and $N(R^4)_2$. Here, $R^2$ and $R^3$ may be identical or different, but the following general conditions must be adhered to:

(d) if $R^2$ is hydroxyl or $N(R^4)_2$, $R^3$ is hydrogen, and
(e) if $R^3$ is $N(R^4)_2$, $R^2$ may also be $N(R^4)_2$.

The two radicals $R^4$ which are bonded to one and the same nitrogen atom may be identical or different. Suitable radicals $R^4$ are branched, straight-chain or cyclic alkyl groups or branched, straight-chain or cyclic aza- or oxaalkyl groups. Furthermore, the two radicals $R^4$ may be cyclically bonded to one another via a divalent group so that, together with the nitrogen atom, they form a heterocyclic structure.

Examples of suitable radicals $R^4$ are methyl, ethyl, propyl, n-butyl, sec-butyl, tert-butyl, n-pentyl, tert-pentyl, neopentyl, n-hexyl, n-heptyl, n-octyl, 2-ethylhexyl, isooctyl, tert-octyl, n-nonyl, n-decyl, 5,5dimethylhexyl, 6,6-dimethylheptyl, 7,7-dimethyloctyl, 8,8-dimethylheptyl, 2,4,4-trimethylpentyl, 3,5,5-trimethylhexyl, 4,6,6-trimethyl-2-(1,3,3-trimethylbutyl)heptyl, 4,5,7,7-tetramethyl-2-(1,3,3-trimethylbutyl)heptyl, 8,8-dimethyl-4,5-bis(3,3-dimethylbutyl)-nonyl,5hydroxyheptyl, 3-azabut-1-yl, 2-azapent-1-yl, 3-azahex1-yl, 3-aza-4,4-dimethylpent-1-yl,3-aza-5,5-dimethylhex1yl, 3-tert-butoxypropyl, 4-tert-butoxypentyl, 6-tert-butoxphexyl, 7-tert-butoxyheptyl,3-tert-butoxy-2-methylpropyl, 3-tert-butoxy-2,3-dimethylpropyl, 3-tert-butoxy2-methyloctyl, 5,5-bis-(tert-butoxy)-3,4-dimethylpentyl, 2-(2-oxa-3,3-dimethylbutyl)-octyl, 2-ethyl-4-(3-oxa-4,4-dimethylpentyl)-8-oxa-9,9-dimethyldec-Yl, 4-(1,3-dioxan2-yl)-butyl, 4-(1,3-dioxan-2-yl)-3-methylbutyl, 4-(1,3-dioxan-2-yl)-4-methylbutyl-, 4-(1,3-dioxan-2-yl)-2,3-trimethylbutyl, 5-(1,3-dioxan-2-yl)-pentyl, 6-(1,3-dioxan-2-yl)-hexyl, 4-(4,4-dimethyl-1,3-dioxacyclooct-2- yl)-butyl, 4-1,3-dioxolan-2-yl)-3-methylbutyl and 6-(5,5-dimethyl-1,3-dioxan-2-yl)-3-ethyl-4,5-dimethylhexyl.

The two radicals $R^4$ on one and the same nitrogen atom can. however. also be bonded cyclically to one another via a divalent group so that the total $N(R^4)_2$ group is a heterocyclic radical.

Examples of suitable heterocyclic radicals which are based on such bonding of the two radicals $R^4$ to one another are morpholin-1-yl, imidazol-1-yl, $\Delta^2$-imidazolin1-yl, pyrrolidin-1-yl, piperid-1-yl, piperazin-1-yl, 4-methylpiperazin-1-yl, indolin-1-yl and isoindolin-1-yl, of which piperid-1-yl and morpholin-1-yl are particularly preferred.

Very particularly preferred radicals $R^4$ are methyl. ethyl, propyl, n-butyl and 3-aza-4,4-dimethylpent-1-yl, of which n-butyl has an outstanding technical effect.

Examples of suitable additives I are the additives I - 1 to I - 18:

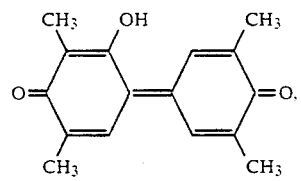

I-1

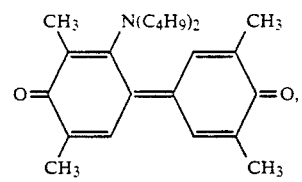

I-2

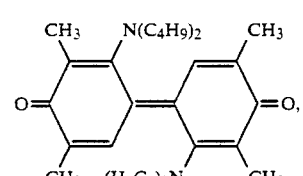

I-3

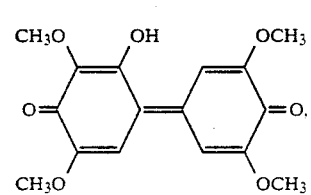

I-4

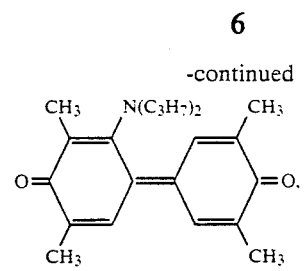

I-5

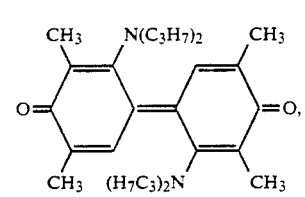

I-6

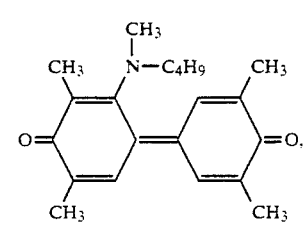

I-7

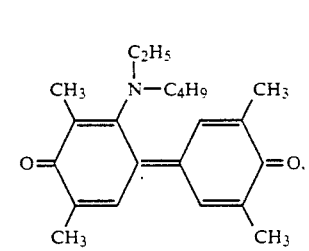

I-8

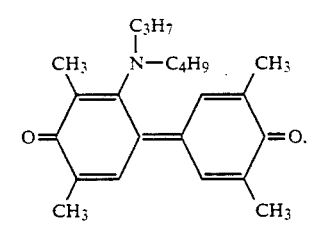

I-9

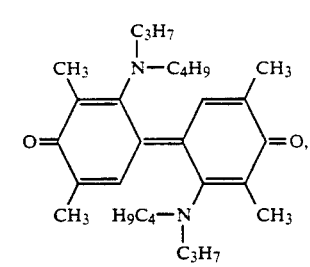

I-10

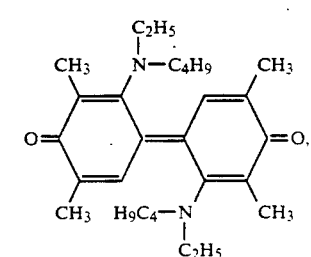

I-11

-continued
I-12 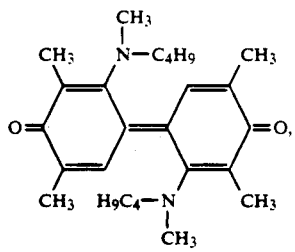
I-13 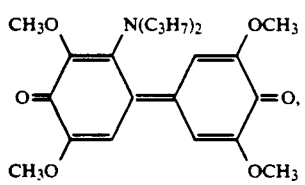
I-14 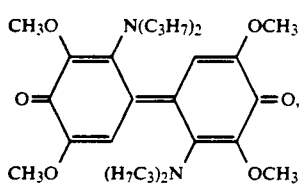
I-15 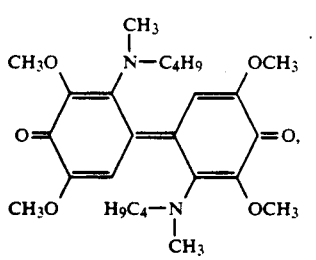
I-16 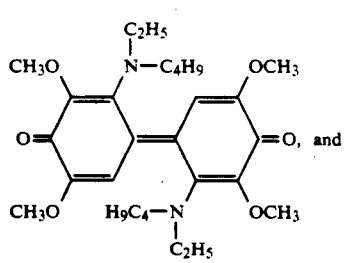, and
I-17 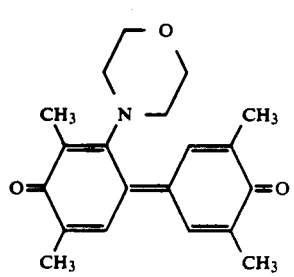
-continued
I-18 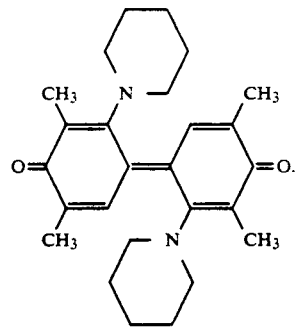
Among these, the novel additives I - 1 and I - 3 are very particularly preferred.
Examples of suitable novel additives II are the additives II - 1 to II - 18
II-1 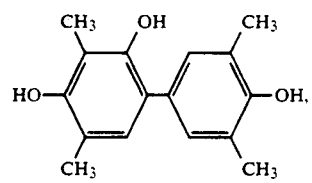
II-2 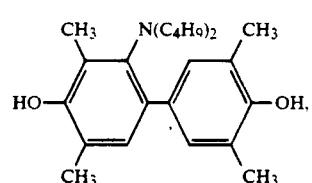
II-3 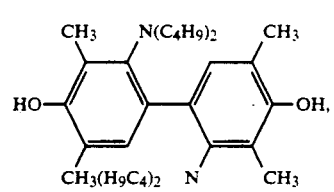
II-4 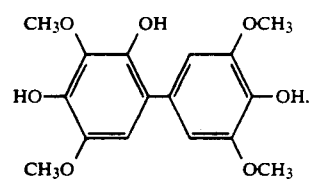
II-5 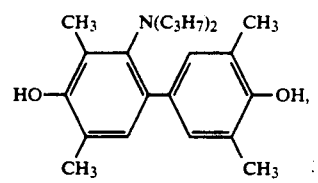
II-6 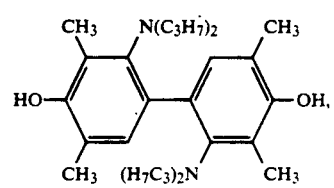

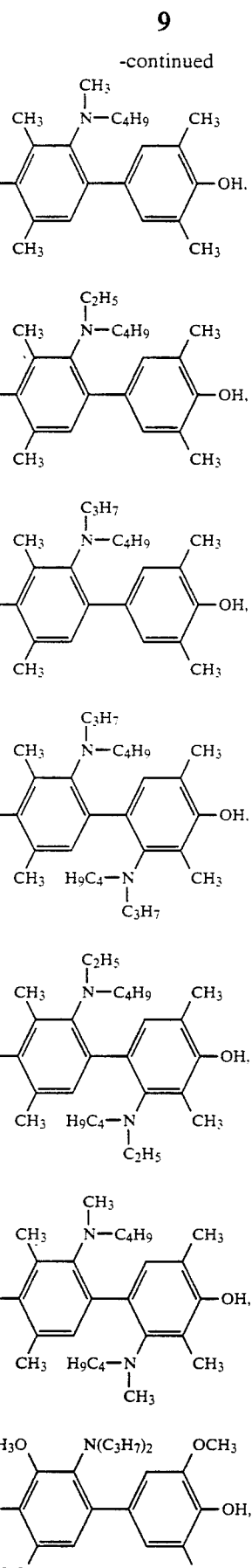
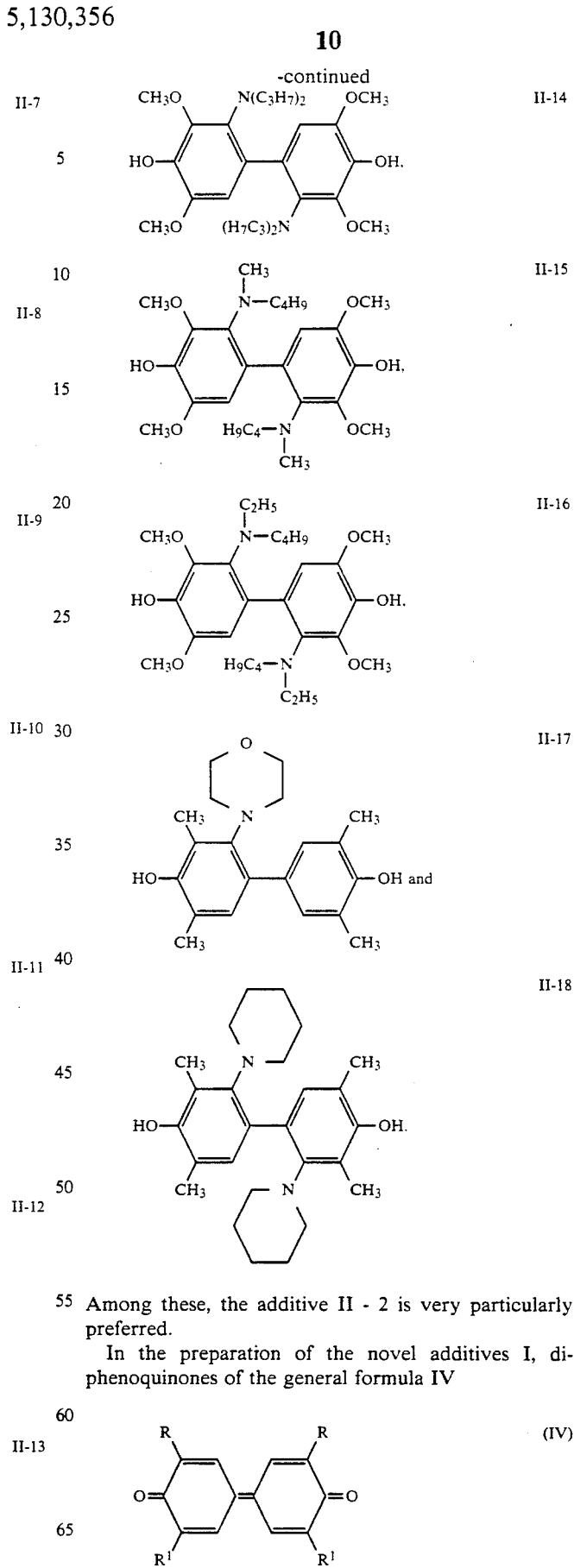
Among these, the additive II-2 is very particularly preferred.
In the preparation of the novel additives I, diphenoquinones of the general formula IV
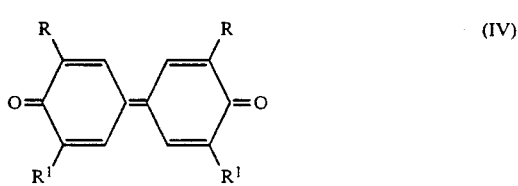

where R and R¹ have the abovementioned meanings, are used as starting materials. The preparation of these diphenoquinones IV is known per se and is carried out, for example, by copper(II)-catalyzed oxidation of the disubstituted phenols of the general formula VII

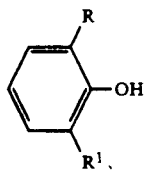

(VII)

in acetonitrile. The diphenoquinones IV obtained in this manner are then converted into the novel additives I, for example by the methods described by Wanzlick, Lehmann-Horchler, Mohrmann, Gritzki, Heidepriem and Pankow in the article Neuere Methoden der Präparativen Organischen Chemie IV, Synthesen mit naszierenden Chinonen, Angew. Chem. 76 (1964), 313-356, in particular 315, for mononuclear quinones.

The novel additives II are obtained from the novel additives I by reduction with a mild reducing agent in the presence of water.

In addition to the novel additives I and/or II, the novel molding or the mixture of which the novel molding consists may contain from 1 to 1,000 ppm, based on its total amount, of one or more further novel additives of the general formula III

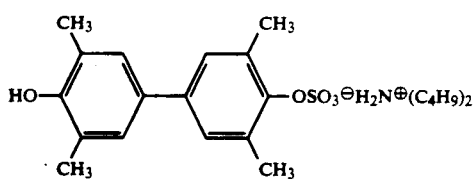

(III)

where R, R¹ and R⁴ have the abovementioned meanings. Although the novel molding or the mixture of which it consists may contain more than 1,000 ppm of one or more novel additives III, these additives display their advantageous technical effect after the addition of only small amounts, so that there is no need for a higher content. Examples of suitable novel additives III are the novel additives III - 1 to III - 10

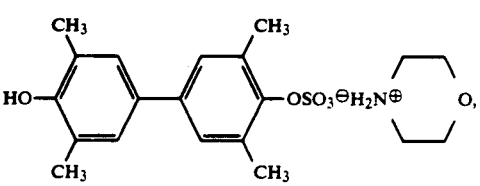
III-1

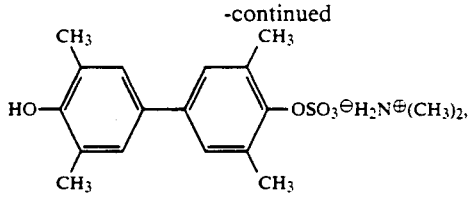
III-2

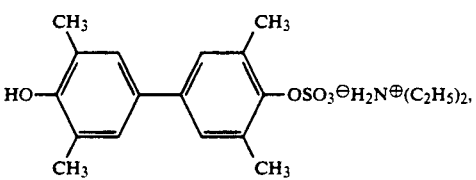
III-3

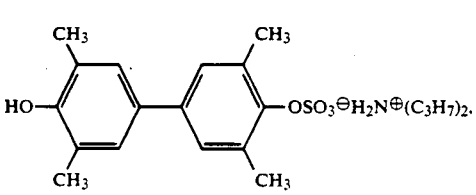
III-4

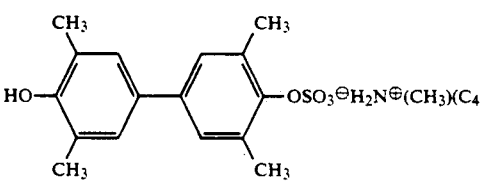
III-5

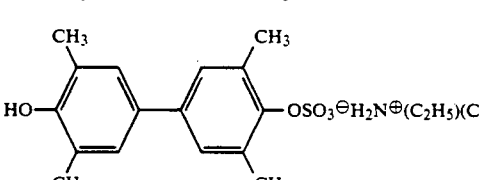
III-6

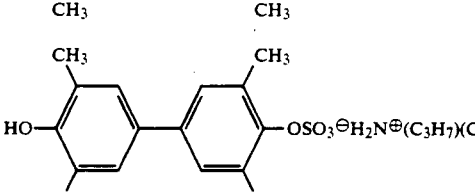
III-7

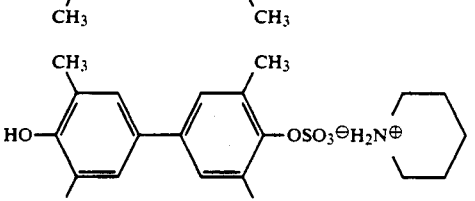
III-8

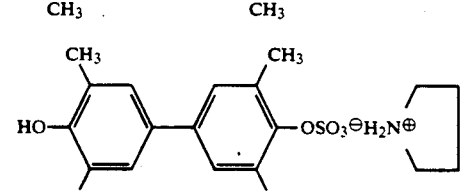
III-9

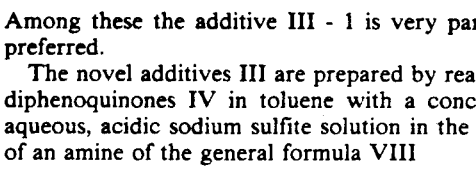
III-10

Among these the additive III - 1 is very particularly preferred.

The novel additives III are prepared by reacting the diphenoquinones IV in toluene with a concentrated, aqueous, acidic sodium sulfite solution in the presence of an amine of the general formula VIII
very

HN(R⁴)₂ (VIII)

where the two radicals R⁴ have the abovementroned meanings. Thereafter, the novel additives III are isolated from the reaction mixture by conventional, known preparative methods and then identified In addition to the novel additives I and/or II and, optionally, III, the novel molding or the mixture of which it consists may contain further additives Examples of further suitable additives are additives of the general formula IV

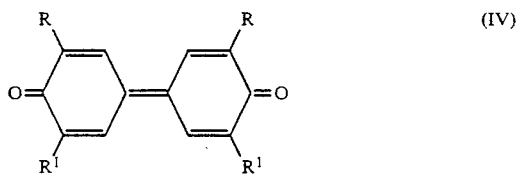

and/or of the general formula V

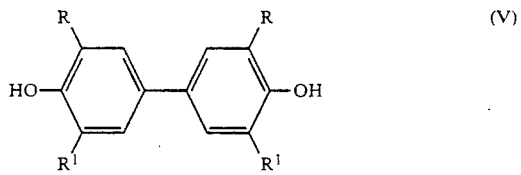

where R and R¹ have the abovementioned meanings. The additives IV and V may be present in the novel moldings or in the mixtures of which they consist in a total amount of from 1 to 10,000 ppm. It is advantageous if the content of additives IV, where they are used, is from 1 to 100 ppm, whereas the content of additives V may be up to 10,000 ppm.

Furthermore, the novel molding or the mixture of which it consists may contain from 10 to 10,000 ppm of oligomeric phenylene ethers of the general formula VI

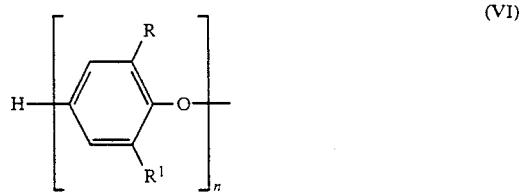

where R and R¹ have the abovementioned meanings and n is an integer from 3 to 15.

Oligomeric phenylene ethers VI are known compounds which can be prepared, for example, via the known rearrangement reaction of disubstituted phenols VII with polyphenylene ethers, conversion of the resulting reaction products to silyl ethers or acetates and subsequent separation by distillation and hydrolysis of the relevant silyl ethers or acetates, or by selective synthesis by the Ullmann reaction.

The novel moldings or the mixtures of which they consist are opaque to light of wavelength $\lambda < 400$ nm and transparent to light of wavelength $\lambda > 400$ nm. The mixture of which the novel molding consists has an intrinsic viscosity $[\eta]$ of from 0.5 to 0.8, preferably from 0.55 to 0.75, in particular from 0.6 to 0.75, measured in 0.5% strength chloroform solution at 25° C.

The novel molding consists predominantly of vinylaromatic polymers and polyphenylene ethers.

Both the vinylaromatic polymers and the polyphenylene ethers may be present in the mixture or in the novel molding as polymers which have been separately prepared and subsequently mixed with one another. However, some or the total amount of the vinylaromatic polymers and polyphenylene ethers may be bonded in the form of block copolymers or comb polymers.

Regardless of whether the vinylaromatic polymers and the polyphenylene ethers are present in the novel molding as polymers which have been separately prepared and subsequently mixed with one another or as block copolymers or as comb polymers, the weight ratio of polyphenylene ethers to vinylaromatic polymers is from 30 : 70 to 50 : 50, in particular from 35 : 65 to 40 : 60.

Advantageous polyphenylene ethers have an intrinsic viscosity $[\eta]$ of from 0.5 to 0.6, measured in 0.5% strength chloroform solution at 25° C. They have a nonuniformity of molecular weight $\overline{M}_w/\overline{M}_n$ of from 4 to 11, in particular from 5 to 10. Particularly advantageous polyphenylene ethers have a number average molecular weight $\overline{M}_n$ of from 3,500 to 7,000, in particular from 4,000 to 6,000. Further particularly advantageous polyphenylene ethers are those which have a weight average molecular weight $\overline{M}_w$ of from 30,000 to 50,000, in particular from 35,000 to 45,000. Very particularly advantageous polyphenylene ethers have both the abovementioned number average molecular weight $\overline{M}_n$ and the abovementioned weight average molecular weight $\overline{M}_w$.

Examples of suitable polyphenylene ethers which meet the abovementioned conditions are polyphenylene ethers of the general formula IX

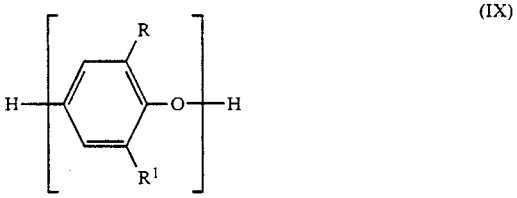

where R and R¹ have the abovementioned meanings, for example
poly-(2,6-dimethylphen-1,4-ylene ether),
poly-(2,6-diethylphen-1,4-ylene ether),
poly-(2,6-diphenylphen-1,4-ylene ether),
poly-(2,6-diethoxyphen-1,4-ylene ether),
poly-(2-methyl-6-chlorophen-1,4-ylene ether),
poly-(2-methyl-6-bromophen-1,4-ylene ether),
poly-(2-methyl-6-isopropylphen-1,4-ylene ether),
poly-(2,6-dimethoxyphen-1,4-ylene ether),
poly-(2-methyl-6-methoxyphen-1,4-ylene ether),
poly-(2-methyl-6-ethoxyphen-1,4-ylene ether) or
poly-[2,6-bis-(4-methylbut-2-en-1-yl)-phen-1,4-ylene ether]of which
poly-(2,6-dimethylphen-1,4-ylene ether) is particularly suitable.

The abovementioned polyphenylene ethers may contain, as copolymerized units, minor amounts, ie. from 0.001 to 5 mol %, of phen-1,4-ylene ether units trisubstituted in the 2,3,6-position, for example 2,3,6-tri-methylphen-1,4-ylene ether units.

Other essential components of the novel molding or of the mixture of which it consists are vinylaromatic polymers. These may be vinylaromatic homopolymers or copolymers which have been prepared by the known free radical polymerization. However, it is also possible to use vinylaromatic homopolymers, copolymers and block copolymers which have been prepared by the conventional known anionic polymerization methods.

The monomers used for the preparation of such vinylaromatic polymers are the conventional, known ones. Styrene, α-methylstyrene, o-, m- and p-methylstyrene are particularly suitable. It is particularly advantageous to use high molecular weight vinylaromatic polymers having a weight average molecular weight $\overline{M}_w$ of from $8 \times 10^4$ to $2 \times 10^6$ together with low molecular weight vinyl-aromatic polymers having a weight average molecular weight $\overline{M}_w$ of from $5 \times 10^3$ to $3 \times 10^4$.

The vinylaromatic polymers may contain from 0.1 to 8% by weight of cyanoethylene groups and/or from 0.01 to 10% by weight of groups of the general formula X

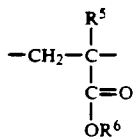 (X)

where $R^1$ is hydrogen or methyl and $R^6$ is a substituted or unsubstituted $C_1$-$C_{10}$-alkyl, $C_5$-$C_8$-cycloalkyl or $C_6$-$C_{10}$-aryl group, the percentages being based on the total amount of the said polymers. Groups of this type are derived from the conventional, known acrylates or methacrylates, which can be particularly readily copolymerized with vinylaromatics, for example the methyl, ethyl, propyl, isopropyl, n-butyl, sec-butyl, tert-butyl, n-pentyl, n-hexyl, n-heptyl, n-octyl, 2-ethylhexyl, nonyl, decyl, cyclopentyl, cyclohexyl, 2-methylcyclohexyl, 2,4-dimethylcyclohexyl, phenyl, 4-methylphenyl or naphthyl ester of acrylic acid or of methacrylic acid.

Furthermore, the vinylaromatic polymers may contain, in addition to the cyanoethylene groups and/or the groups X or instead of these, from 0.01 to 10% by weight, based on their total amount, of groups of the general formula XI

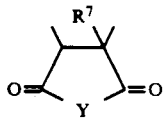 (XI)

where $R^7$ is hydrogen or methyl and Y is oxygen, N-$C_1$-$C_6$-alkylimino or N-$C_6$-$C_{10}$-arylimino. These groups XI are derived from monomers such as maleic anhydride, itaconic anhydride or N-methyl-, N-ethyl-, N-propyl-, N-butyl-, N-pentyl-, N-hexyl-, N-phenyl- or N-naphthylmaleimide or -itaconimide, which are known to be very suitable for copolymerization with vinylaromatics.

The cyanoethylene groups, the groups X and/or the groups XI may be present in the vinylaromatic polymer main chains as randomly distributed monomer units. However, they may also form pure oligomeric or polymeric blocks which can be incorporated in the vinylaromatic polymer main chains and/or can be bonded to these main chains as side radicals. The stated groups can, however, also form the monomer units of oligomeric or polymeric homo- or copolymers or of block or graft copolymers which have been prepared separately and then added to the vinylaromatic polymers. In addition, the stated groups may form polymer chains which carry vinylaromatic polymer side chains.

Regardless of the form in which the cyanoethylene groups, the groups X and/or the groups XI are present in the novel molding, the abovementioned weight ranges are applicable for these groups. Examples of particularly suitable vinylaromatic polymers are polystyrene, poly-αmethylstyrene, poly-p-methylstyrene, copolymers of styrene and α-methylstyrene, copolymers of styrene and p-methylstyrene and copolymers of styrene, α-methylstyrene and p-methylstyrene or styrene/methyl methacrylate copolymers.

Vinylaromatic polymers of the abovementioned type which may contain the cyanoethylene groups, the groups X and/or the groups XI are conventional known ones.

The novel molding or the mixture of which it consists may contain from 0.05 to 10% by weight, based on its total amount, of additives such as antioxidants, plasticizers, lubricants and dyes. Additives of this type are the conventional known ones. Particularly suitable ones are those which can be distributed in molecular disperse form in the mixture and absorb light of wavelength λ of from 720 to 1,000 nm only weakly if at all.

Examples of particularly suitable additives of this type are tert-butylcresol, white oil and zinc stearate.

The particularly advantageous novel molding contains, in the main, based on a total of 100 parts by weight, from 30 to 50, in particular from 35 to 40, parts by weight of poly-(2,6-dimethylphen-1,4-ylene ether) per 50-70, in particular 60-65, parts by weight of a mixture of, based on the mixture, from 68 to 97% by weight of polystyrene having a weight average molecular weight $M_w$ of from $8 \times 10^4$ to $10^6$ and from 3 to 25% by weight of a random copolymer and up to 7% by weight of further ingredients, such as plasticizers and antioxidants, said random copolymers consisting of from 2 to 98% by weight of copolymerized α-methylstyrene and from 98 to 2% by weight of copolymerized p-methylstyrene having a weight average molecular weight $N_w$ of from $7 \times 10^3$ to $2 \times 10^4$. In addition, the particularly advantageous novel molding always contains one or more of the novel additives I - 1, I - 3 and II - 2 in an amount of from 1 to 1,000 ppm.

Furthermore the novel molding may contain the novel additives III, in particular the novel additive III - 1, in an amount of from 1 to 1,000 ppm.

The novel molding has many particular advantages. It is particularly suitable for optical purposes where optical transparency and isotropy of moldings and freedom of moldings from orientation birefringence are especially important. The novel molding may have any external shape which arises directly from its intended use. Because of its particularly advantageous properties, the novel molding can be used especially as a carrier of digital or analog data For this purpose, it has the shape of a circular disk having a central hole and a diameter of from 50 to 300 mm.

The novel molding in the form of a circular disk having a central hole may have two planar surfaces. However, one or both of these two surfaces may have a relief structure in the micrometer and/or submicrometer range. Such novel moldings or circular disks having a central hole are used in particular as dimensionally stable substrates for audio compact disks (CD), audiovisual compact disks (CDV) and laser-optical and magnetooptical computer disks. The novel moldings in the form of such circular disks having a central hole are referred to below as novel dimensionally stable substrates.

Very particularly advantageous novel dimensionally stable substrates have a surface with a relief structure in the micrometer and/or submicrometer range.

These relief structures serve for exact guidance of laser beams with which the digital data contained in the relevant audio compact disks (CD), the audiovisual compact dis.ks (CDV) and the laser-optical and magnetooptical computer disks are read. The relief structures ensure rapid and precise response of the track position servomechanisms and autofocusing means in the laser-optical write and read heads of the disk drives, for example in CD players. The relief structures therefore permit or improve tracking. Moreover, the relief structures may themselves constitute data, as is the case, for example, in the audio compact disks (CD) and the audio-visual compact disks (CDV). The relief structures can, however, also be used for coding data which are recorded with the aid of write laser beams in the recording layers of laser-optical and magneto-optical computer disks.

In principle, the relief structures consist of raised parts and/or of indentations. Both may be in the form of continuous, concentric or spiral tracks or in the form of isolated protuberances and/or holes Furthermore, the relief structure may have a more or less smooth wave form. The tracks are preferred here. In their transverse direction, they have a rectangular sawtooth-like, V-shaped or trapezoidal contour. The indentations are referred to in general as grooves and their raised parts as land. Tracks having 50–200 nm deep and 0.4–0.8 $\mu$m wide grooves separated by a 1–3 $\mu$m wide land are particularly advantageous here.

The novel dimensionally stable substrates, each possessing a surface having relief structures, furthermore have the particular advantage that they are very useful for the production of audio compact disks (CD), audiovisual compact disks (CDV) and laser-optical and magneto-optical computer disks having a sandwich structure. For the production of the sandwich structure, two novel dimensionally stable substrates are placed exactly centrally one on top of the other in pairs and are connected to one another in such a way that their surfaces which have relief structures and which either already contain the digital data or carry laser-optical or magneto-optical recording layers are parallel to one another and face one another, there being a certain distance between these two surfaces. This distance can be set in a conventional known manner with the aid of spacers, such as rings, webs or small columns. These spacers may also provide a gas-tight seal for the space between the two surfaces having relief structures, provided that the said spacers are in the form of rings. Moreover, the two dimensionally stable substrates may be connected to one another in their middle by means of a hub.

Both the spacers and the hub may be suitable moldings of any composition. However, it is particularly advantageous if both the spacers and, if it is used, the hub are novel moldings having the suitable external shape. The individual novel moldings may be firmly bonded to one another with the aid of suitable adhesives. However, it is advantageous to join the novel moldings by the known technique of ultrasonic welding.

Furthermore, two of these novel dimensionally stable substrates, each of which has a surface possessing relief structures, can be placed exactly one on top of the other in pairs, centered, and firmly bonded to one another over the entire surface, so that their surfaces having the relief structures face either outward or inward.

The novel dimensionally stable substrates are produced by the conventional shaping methods known from the prior art. Shaping the novel mixtures of which the dimensionally stable substrates according to the invention consist, by injection molding is advantageous here. For this purpose, the novel mixture is prepared in an extruder and transported therein, in the form of a melt, to an injection molding chamber having a suitable shape, in which it is injection molded to give the dimensionally stable substrate of the desired three-dimensional shape. In this process, the relief structure is impressed, by means of a die of suitable shape present in the injection molding chamber, in the surface of the relevant novel dimensionally stable substrate to be produced. This process is usually carried out under cleanroom conditions.

Depending on the intended use, the novel dimensionally stable substrates are further processed in various ways and have further particular advantages:

If the dimensionally stable substrates are used as audio compact disks (CD) and as audiovisual compact disks (CDV), their surface possessing relief structures is generally provided with a metal mirror to improve reflection of the laser beams Further layers, for example protective layers, can then be applied to this metal mirror in a conventional known manner. The compact disks obtained in this manner have a particularly outstandingly shaped relief structure which corresponds exactly to the original on the die. The compact disks therefore have a particularly low bit error rate and a particularly high signal-to-noise ratio. They therefore have extremely high playback quality. Moreover, these compact disks can be visually identified in a simple manner on the basis of the coloring of the novel dimensionally stable substrates.

If the said substrates are used as substrates of recording layers of laser-optical computer disks, their surface possessing relief structures is provided with a conventional known, generally amorphous, thermally alterable recording layer, if necessary via conventional known intermediate layers. The said recording layer may consist of any substance. Dyes, tellurium and gold may be mentioned as examples It is known that the digital data in this amorphous, thermally alterable recording layer are recorded with the aid of a pulse-modulated write laser beam having a beam diameter of from 300 to 2,000 nm, a beam power of from 1 to 20 mW, a pulse duration of from 10 to 1,000 ns and a write wavelength $\lambda$ of from 400 to 1,000 nm. It is known that the write laser beam is moved over the recording layer during the write process. The thermally alterable areas of the recording layers therefore generally have a circular or elliptical basic shape Depending on the composition of the recording layer, the thermally alterable areas may be holes (ablative data recording), pits which may have a well defined wall (deformative data recording) or areas in which irradiation has caused a phase transition in the material, producing other modification (data recording through phase transition). Alternatively, the recording layer may have underneath layers which expand or evolve gases on irradiation, with the result that the recording layers are locally expanded and relief structures which contain the recorded digital data form in the surface of the recording layer. However, the gases may also be liberated in the recording layer itself with formation of small light-scattering bubbles (vesicular data recording). Furthermore, a chemical reaction of a component or a chemical reaction between a plurality of components of the recording layer may have taken place in the thermally alterable areas, or the thermally alterable areas may have formed through enlargement or fusion of small particles.

Regardless of the specific mechanisms which govern the formation of thermally alterable areas during irradiation with write laser beams, the said areas have a different reflectivity for laser beams compared with the thermally unchanged areas, which is utilized for detecting recorded data. For this purpose, a read laser beam having a beam power of from 0.1 to 2 mW and a wavelength $\lambda$ of from 400 to 1,000 nm is moved over the recording layer, which it strikes at right angles or obliquely. When it strikes the recording layer at right angles it can be focused and when it strikes the said layer obliquely it must be focused. If the read laser beam encounters a thermally altered area during scanning of the recording layer, the properties of the light reflected or transmitted by the recording layer change, and this can be detected with the aid of suitable detectors. Suitable apparatuses which can be used for recording on laser-optical computer disks and for reading them are the conventional known laser-optical disk drives.

Since, in laser-optical recording and reading of data, the recording layers are advantageously exposed through the dimensionally stable substrate, the particular advantageous properties of the novel dimensionally stable substrates are particularly apparent here: they permit exposure of thermally alterable recording layers to laser beams of a very wide range of wavelengths, the intensity of the said beams being adversely affected in a scarcely noticeable manner if at all. Moreover, they protect UV-sensitive thermally alterable recording layers from destruction by UV light, which destruction may occur on prolonged storage of the laser-optical computer disks in daylight The laser-optical computer disks which contain the novel dimensionally stable substrates accordingly have a longer life, better corrosion resistance, higher playback quality, a lower bit error rate and a higher signal-to-noise ratio than laser-optical computer disks which contain conventional known dimensionally stable substrates.

When the novel dimensionally stable substrates are used as substrates in magneto-optical computer disks, their surface possessing relief structures is covered with a conventional known magneto-optical recording layer. This may be an amorphous ferrimagnetic lanthanide transition metal alloy layer magnetized at right angles to its surface. The thermally altered areas recorded in these recording layers are in the form of spots which have a direction of magnetization opposite to the original direction. They are formed during heating of the amorphous ferrimagnetic material of these layers by the write laser beam under the influence of an applied magnetic field. As a result of the heating, the coercive force $H_c$ of the amorphous ferrimagnetic material decreases. If the coercive force $H_c$ falls below the field strength of the applied magnetic field at a critical temperature dependent on the particular material used, the relevant area undergoes magnetic reversal These areas are read using linearly polarized light of a continuous-wave laser whose light output is not sufficient to heat the material above the critical temperature. This laser beam is reflected either by the recording layer itself or by a reflector layer arranged behind it, interaction occurring between the magnetic moments in the recording layer and the magnetic vector of the laser lightwave. As a result of this interaction, the plane of polarization E,rar/E/ of the reflected laser light is rotated through a small angle from the original plane, this also being referred to as the Kerr effect or Faraday effect This rotation of the plane of polarization e,rar/E/ of the reflected laser light can be measured and converted into signals with the aid of suitable optical and electronic apparatuses. Since, in this method of recording, the magneto-optical recording layer is usually irradiated through the dimensionally stable substrate, a physical effect critical for reading of the data, ie. the rotation of the plane of polarization of the laser light, being small, the particular advantages of the novel dimensionally stable substrates are very particularly evident here. For example, the magneto-optical computer disks which contain the novel dimensionally stable substrates have a longer life, a lower rate of corrosion, a lower bit error rate and a higher signal-to-noise ratio than magneto-optical computer disks which contain the conventional known dimensionally stable substrates.

EXAMPLES AND COMPARATIVE EXPERIMENTS

The particular advantages of the novel moldings are described below by way of example, with reference to dimensionally stable substrates for laser-optical computer disks.

In the Examples and Comparative Experiments which follow, the thickness of the individual recording layers was determined from scanning electron micrographs.

The signal-to-noise ratio in dB was determined in a known manner for laser-optical computer disks on which data had been recorded with the aid of a pulse-modulated laser (wavelength $\lambda$ of emitted light: 830 nm; pulse duration: 500 ns; light output: 6 mW) through the dimensionally stable substrate. For this purpose, the laser-optical computer disks were read with the aid of a continuous-wave laser (wavelength $\lambda$ of emitted light: 780 nm; light output: 0.5 mW) through the dimensionally stable substrate The emitted read laser beam was always moved over the laser-optical computer disks at a relative speed of 4 m/sec. All the light reflected by the laser-optical computer disks was collected and analyzed.

The recording sensitivity (nJ), ie. the minimum light output of the write laser beam above which satisfactorily readable thermally altered bits are produced in a recording layer, was determined by conventional known methods of measurement.

In the Examples and Comparative Experiments which follow, dimensionally stable substrates which contained conventional known, concentric tracks on one surface were used. Their indentations are generally referred to as grooves and their raised parts are generally referred to as land. It is known that the tracks are used for exact guidance of the read and write laser beams which are emitted by the laser-optical write and read head of the disk drive. For this purpose, it is necessary for the track position servomechanisms in the laser-optical head to receive sharp optical signals These signals are produced by diffraction of the laser light reflected by computer disks, generally to the laser-optical head, at the boundary between groove and land, the conventional known photodiode arrangements being used for detection and analysis of these light signals For the tracking characteristics, ie. exact guidance, in particular of the read laser beams, high optical contrast between land and groove is essential since otherwise weak and broadened signals are obtained, if any at all. The latter is often the case in laser-optical computer disks on which data has been recorded However, this leads to a low signal- to-noise ratio and generally makes it more difficult to find recorded data The width of the signals and the difference between the intensity of the laser light reflected back by a groove and of that reflected back by a land are therefore generally taken as a measure of the quality of tracking. An additional quality criteria is whether this intensity difference is constant and high over the entire diameter of a laser-optical computer disk.

Accordingly, the tracking characteristics of the laser-optical computer disks were determined below by reading the materials with a read laser beam ($\lambda = 780$ nm, light output: 0.5 mW) transverse to the tracks. Measurement was carried out over the entire diameter of the laser-optical computer disks. The laser light reflected back was collected with the aid of conventional known optical arrangements, fed to photodiodes and converted by means of suitable electronic modules into electrical signals, whose height was plotted as a function of the computer disk diameter. An assessment was made as to whether the differences between the height of the signals obtained from the lands and that of the signals obtained from the grooves were constant, well defined and high over the entire diameter of the laseroptical computer disks, and the tracking characteristics were rated as follows on the basis of this assessment:
Very good
Well defined signals; large difference between the heights of the land signals and the groove signals which is constant over the entire diameter;
Good
Well defined signals; large difference between the relevant signal heights which however varies to a greater or lesser extent over the entire diameter;
Unsatisfactory
Broad, poorly defined signals; small difference between the relevant signal heights; this difference may also vary to a greater or lesser extent over the entire diameter; or
Poor
No difference between the relevant signal heights To check whether recording on the laser-optical computer disks results in a change in the tracking characteristics, both laser-optical computer disks on which no data had been recorded and those on which data had been recorded were measured and rated in the manner described above. If there were marked differences in the tracking rating of a laser-optical computer disk in the unrecorded state on the one hand and in the recorded state on the other, this is a serious disadvantage. If the difference in ratings was small starting from a very good or good level, this confirmed the particular advantageous properties of the relevant laser-optical computer disk.

The uncorrected bit error rate was determined in a conventional known manner by recording standard information on the laser-optical computer disk and reading the data, a time interval analyzer, TIA, being used. The said disks were read directly after data had been recorded on them (first reading).

The laser-optical computer disks were stored for several weeks in daylight and then read again (second reading) in order to determine whether there was any deterioration in the properties as a result of storage.

EXAMPLE 1

Preparation of the novel additives I; general experimental methods:
Method A 10 g of a diphenohydroquinone of the general formula V were dissolved in 100 ml of acetone. 7 g of silver oxide and 10 g of ignited sodium sulfate were added to the resulting solution. The resulting mixture was cooled to 0° C., after which 2 ml of a secondary amine of the general formula $HN(R^4)_2$ (VIII) or 10 ml of a concentrated solution of a solid secondary amine of this general formula in acetone were added. The resulting reaction mixture was then thoroughly mixed. After standing for from 10 minutes to 2 hours, the solution of the reaction products was separated off from the solid organic components present therein and evaporated down. The crude product thus obtained was analyzed by high pressure liquid chromatography (HPLC) in combination with mass spectrometry. The HPLC column used was the reverse phase nucleoside 120-5 C18 from Machery and Nagel. The eluant used was a methanol/water mixture whose water content increased steadily during elution of the crude products applied to the column. The wavelength $\lambda$ of the UV light used for detection was 420 nm.

For the novel additive I-3

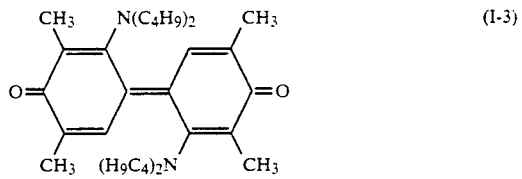

a retention time of 20.8 minutes was determined by the abovementioned method. The mass spectrum showed a molecular peak at m/e 494, in agreement with the theoretical value.
Method B 15 g of a diphenoquinone of the general formula IV were suspended in 500 ml of toluene, and a mixture of 39 g of a secondary amine of the general formula $HN(R^4)_2$ (VIII) and 0.72 g of CuBr was added. The mixture was then gassed with a stream of 50 l/h of oxygen for 3 hours with thorough stirring, and the gas space above the mixture was simultaneously flushed with nitrogen. After the end of the reaction, the resulting solution of the reaction products was separated off by filtration from the solid components present therein. Thereafter, the solution was extracted with an aqueous solution of disodium ethylenediaminetetraacetate in order to remove dissolved copper compounds. The purified solution of the reaction products was further processed as described in Method A.

For the novel additive I - 3, which had been prepared by Method B, the measurement results obtained were the same as those stated in Method A.
Method C Method C is substantially the same as Method B, the only difference being that in Method C 5 ml of aqueous concentrated ammonia were used instead of the secondary amine of the general formula $HN(R^4)2$ (VIII).

For the novel additive I - 1

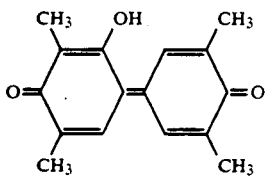
(I-1)

obtained here, a retention time of 17 minutes and, in agreement with the theoretical value, a molecular peak at m/e = 256 were determined by the methods of measurements stated in Method A.

EXAMPLE 2

Preparation of the novel additives II: general experimental method:

The novel additives II were obtained in a very simple manner by reducing the additives I (cf. Example 1) with mild reducing agents.

For this purpose, 20 g of a novel additive I were initially taken with 20 g of $SnCl_2 \cdot 2H_2O$ in 200 ml of acetone. 17 ml of concentrated hydrochloric acid were added dropwise to this mixture in the course of 5 minutes. After a further 10 minutes' reaction time, the mixture was allowed to cool to room temperature and the resulting novel additive II was precipitated by adding 1 l of water, filtered off, washed and dried.

The novel additives II - 1 and II - 3 obtained virtually quantitatively in this manner from the novel additives I - 1 and I - 3 (cf. Example 1) were investigated by IR spectroscopy, mass spectroscopy, mass spectrometry, chromatography and elemental analysis The results obtained in the physical investigations confirmed the previously assumed structure of the novel additives II 1 and II - 3, and the results of the elemental analyses were in very good agreement with the theoretical values.

EXAMPLE 3

Preparation of the novel additives III: general experimental method:

10 g of a secondary amine of the general formula $HN(R^4)_2$ (VIII) and 10 g of a diphenoquinone of the general formula IV were added under nitrogen to 100 g of a 21.7% strength aqueous sodium sulfite solution which had been brought to pH 6 by the addition of 60.1 g of 10% strength hydrochloric acid (1.65 millimoles). The resulting mixture was covered with a layer of 200 ml of toluene. Thereafter, the two-phase reaction mixture was heated at 80° C. for 4 hours, the diphenoquinone IV becoming decolorized with formation of a white solid which separated out at the phase boundary. After the end of the reaction, the aqueous phase had a pH of 5.7.

First, the white solid was separated off from both the aqueous and the organic phase The organic phase was then separated off from the aqueous phase and was evaporated down, a further solid fraction resulting. The two solid fractions were then combined The crude product obtained in this manner was dissolved in 60 ml of hot methanol, the small amounts of methanol-insoluble solids which remained behind being separated off. First the diphenohydroquinone of the general formula V crystallized out from the methanolic solution on cooling to room temperature and was separated off. The methanolic mother liquor was evaporated to dryness under reduced pressure from a water pump, with the result that a major part of the amine of the general formula $HN(R^4)_2$ (VIII) was removed. The remaining residue was recrystallized twice more from methanol in order further to decrease the concentration of diphenohydroquinone V. The novel additive III was isolated with the aid of preparative column chromatography from the crude product obtained in this manner.

3,3,,5,5'-Tetramethyldiphenoquinone was reacted with sodium sulfite in the presence of di-n-butylamine by this general method, 1.6 g of the novel additive III - 1

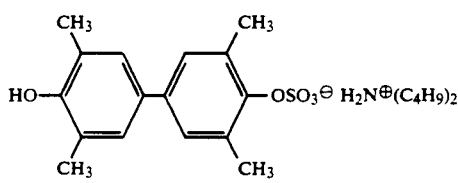

being obtained. The novel additive III 1 was dentified by elemental analyses, which were in agreement with the theoretical values, and by nuclear magnetic resonance spectroscopic measurements. Table 1 below gives an overview of the nuclear magnetic resonance spectroscopic data of the novel additive III - 1.

TABLE 1

Nuclear magnetic resonance spectroscopic data of the novel additive III - 1 (24° C. tetramethylsilane, in $CDCl_3$)

| Shift | Intensity | Assignment |
|---|---|---|
| $^{13}C$ nuclear magnetic resonance spectroscopic data | | |
| 16.2 ppm | 2 | —$CH_3$ |
| 17.6 ppm | 2 | —$CH_3$ |
| 123.8 ppm | 2 | >C= |
| 126.9 ppm | 2 | —CH= |
| 127.0 ppm | 2 | —CH= |
| 132.5 ppm | 1 | >C= |
| 132.7 ppm | 2 | >C= |
| 138.2 ppm | 1 | >C= |
| 148.4 ppm | 1 | >C= |
| 152.1 ppm | 1 | >C= |
| $^1H$ nuclear magnetic resonance spectroscopic data | | |
| 2.27 ppm | 6 | —$CH_3$ |
| 2.45 ppm | 6 | —$CH_3$ |
| 7.11 ppm | 2 | —CH= |
| 7.16 ppm | 2 | —CH= |

EXAMPLES 4 AND 5 AND COMPARATIVE EXPERIMENT V1

Preparation and properties of novel (Examples 4 and 5) and conventional (Comparative Experiment V1) moldings or dimensionally stable substrates; general experimental method:

For Examples 4 and 5 and Comparative Experiment V1, mixtures of vinylaromatic polymers and polyphenylene ethers were prepared under exactly comparable conditions. For this purpose, the vinylaromatic polymers were melted in a twin-screw devolatilization extruder in all cases, and the polyphenylene ether was metered into the particular melt as a 60% strength solution in toluene, the additives being introduced into the melts together with the solutions of polyphenylene ether in toluene.

The resulting mixtures were homogenized in the twin-screw devolatilization extruder during a residence time of one minute with devolatilization at 280° C, discharged from the extruder and converted into granules.

The granules predried at 100° C were injection molded to dimensionally stable substrates under clean-room conditions in a 90 tonne injection molding machine and special mold for shaping dimensionally stable substrates of laser-optical computer disks During this procedure, concentric tracks were impressed on one side of the dimensionally stable substrates by means of a nickel die inserted into the injection mold. The dimensionally stable substrates were 1.2 mm thick and had a diameter of 130 mm. The impressed tracks were 70 nm deep and 0.6 μm wide (groove) with a spacing of 1.6 μm (land).

For each of the three mixtures, the optimum injection molding parameters were set, optimization being effected mainly with regard to planarity of the dimensionally stable substrates and minimum birefringence between crossed polarizers. Table 2 gives an overview of the injection molding parameters of the mixtures and the property profile of the dimensionally stable substrates produced therefrom.

The following mixtures were used for Examples 4 and 5 and Comparative Experiment V1:

EXAMPLE 4

30.0 kg of polystyrene prepared by free radical polymerization and having a weight average molecular weight $\overline{M}_w$ of $1.65 \times 10^5$, 1.5 kg of a copolymer of α-methylstyrene (10% by weight) and para-methylstyrene (90% by weight), having a weight average molecular weight $\overline{M}_w$ of $9 \times 10^3$, 18.5 kg of poly-(2,6-dimethylphen-1,4-ylene ether) having the following specifications intrinsic viscosity $[\eta] = 0.545$ (measured in 0.5% strength solution in chloroform at 25° C.), number average molecular weight $\overline{M}_n$ of $5.5 \times 10^3$, weight average molecular weight $\overline{M}_w$ of $4.1 \times 10^4$, nonuniformity of molecular weight (e,ovs/M/$_w$/$\overline{M}_n$) = 7.4, 1.1 g of 3,3,,5,5,-tetramethyldiphenoquinone (additive IV), 120 g of 3,3,,5,5,-tetramethyldiphenohydroquinone (additive V), 0.3 g of oligo-(2,6-dimethylphen-1,4-ylene ether) having a degree of oligomerization of from 3 to 10 (additives VI), 4 g of additive I - 3

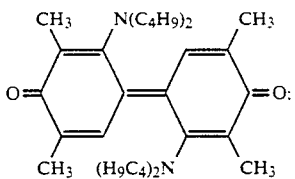

2.1 g of additive III - 1

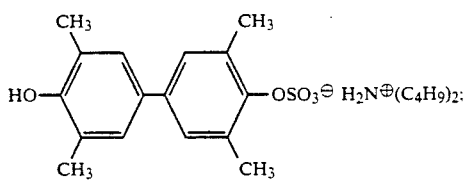

and
60 g of p-tert-butylcresol.

EXAMPLE 5

30.0 kg of polystyrene as in Example 4, 1.5 kg of a copolymer of α-methylstyrene and p-methylstyrene as in Example 4, 18.5 kg of poly-(2,6-dimethylphen-1,4-ylene ether) having the following specifications: intrinsic viscosity $[\eta] = 0.5$ (measured in 0.5% strength solution in chloroform at 25° C.), number average molecular weight $\overline{M}_n$ of $1.65 \times 10^4$, weight average molecular weight $\overline{M}_w$ of $3.25 \times 10^4$, nont 5 uniformity of molecular weight $(\overline{N}_w/\overline{M}_n) = 2.0$, 0.3 g of additive IV according to Example 4, 1 g of additive V according to Example 4, 4.5 g of additive I - 3, 25 g of additive I - 1

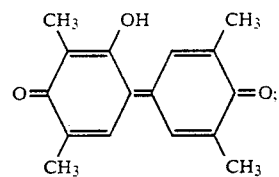

3.4 g of additive III - 1 and
60 g of p-tert-butylcresol.

COMPARATIVE EXPERIMENT V1

31.5 kg of polystyrene as in Example 4,
18.5 kg of poly-(2,6-dimethylphen-1,4-ylene ether) having the specification of Example 5,
0.3 g of additive IV according to Example 4,
11.5 g of additive V according to Example 4 and 60 g of p-tert-butylcresol.

TABLE 2

| Injection molding parameters of the mixtures and property profiles of the dimensionally stable substrates produced therefrom | | | | |
|---|---|---|---|---|
| Injection molding parameters and properties of the substrates | | Example 4 | Example 5 | Comp. Experiment V1 |
| Melt flow index MFI according to DIN 53,735 of the mixtures at 300° C. and under an applied force of 5 kp | (g/10 min) | 96 | 83 | 67 |
| Intrinsic viscosity [η] of the mixtures (0.5%, CHCl₃, 25° C.) | (dl/g) | 0.734 | 0.689 | 0.695 |
| Injection rate of the mixtures | (mm/sec) | 120 | 105 | 90 |
| Optimum injection temperature for the mixtures | (°C.) | 330 | 335 | 350 |
| Maximum birefringence of the | (nm) | 2 | 2 | 20 |

TABLE 2-continued

Injection molding parameters of the mixtures and property profiles
of the dimensionally stable substrates produced therefrom

| Injection molding parameters and properties of the substrates | | Example 4 | Example 5 | Comp. Experiment V1 |
|---|---|---|---|---|
| substrate in the radial range from 25 to 60 mm | | | | |
| Track shape on the surface of the substrate (visual evaluation) | | Very good | Very good | Satisfactory |
| Planarity of the substrates | | Very good | Very good | Satisfactory |
| Maximum temperature of the substrates in sustained use | (°C.) | 125 | 125 | 125 |
| Transparency to light of wavelength λ: | | | | |
| <400 nm | | Opaque | Opaque | Opaque only from 370 nm |
| >400 nm | | Transparent | Transparent | Transparent |

As shown by the comparison, the novel dimensionally stable substrates of Examples 4 and 5 show many improvements compared with those of Comparative Experiment V1: the reduction in the melt viscosity leads to a decrease in the injection temperature and to less thermal damage to the mixtures. Furthermore, shaping in the mold is substantially improved without the maximum temperature in sustained operation being reduced. The reduction in the orientation birefringence to values which are virtually impossible to measure is particularly noteworthy. The novel substrates have advantages even with regard to the yellowness index (YI) of the substrates. Moreover, the novel substrates are opaque even to light of wavelength $\lambda = 400$ nm, whereas the known dimensionally stable substrate does not filter out the harmful short-wavelength light until $\lambda = 370$ nm. Within Examples 4 and 5 themselves, there is also a differentiation between the melt flow indices MFI, the injection rates and the optimum injection temperatures of the mixtures and the yellowness indices (YI) of the novel dimensionally stable substrates, from which it can be concluded that the novel mixture and substrate of Example 4 constitutes an optimum and is therefore even further removed from the prior art than the novel mixture and substrate of Example 5, which in any case are advantageous. Furthermore, the formation of cross-linked gel particles was observed in the substrates of Comparative Experiment V1. In addition, in obliquely incident light, the substrates of Comparative Experiment V1 exhibited in their surface a pearlescent shimmer, which is a disadvantage in view of the fact that these substrates are used in laser-optical and, more so, in magneto-optical computer disks.

EXAMPLES 6 AND 7 AND COMPARATIVE
EXPERIMENT V2

Preparation and properties of laser-optical computer disks having novel (Examples 6 and 7) and known (Comparative Experiment V2) dimensionally stable substrates; general experimental method Two of the dimensionally stable substrates from Examples 4 and 5 (for Examples 6 and 7) and two known dimensionally stable substrates from Comparative Experiment V1 (for Comparative Experiment V2) were coated on a spincoating apparatus at 3,000 revolutions/m.lnute with propanolic solutions which each contained 4% by weight, based on the solution, of a mixture of a dye which absorbs at the wavelengths λ of from 700 to 850 nm and a solution polymer of methyl methacrylate and methacrylic acid.

The weight ratio of dye to polymer was 70 : 30. The dye used was a conventional known triquinocyclopropane dye. Drying gave laser-optical computer disks having amorphous, thermally alterable recording layers which were about 100 nm thick and whose reflectivity for light of wavelength $\lambda = 780$ nm was determined in a known manner as 19% (measurement through the dimensionally stable substrates).

Two identical laser-optical computer disks in each case were firmly joined to one another in the form of a sandwich with the dye layers facing inward, via a spacer ring of 300 μm thickness, by means of an acrylate adhesive.

Spacer rings used here were themselves produced by injection molding of the mixtures of which the dimensionally stable substrates used in each case consisted. Accordingly, the mixture according to Example 4 was used for Example 6, the mixture according to Example 5 for Example 7 and the mixture according to Comparative Experiment V1 for Comparative Experiment V2.

Digital data were recorded in the grooves of laser-optical computer disks on a disk drive. The data were then read (first reading) The results obtained are shown in Table 3.

The laser-optical computer disks were then stored for 3½ weeks in daylight and then read again (second reading). The results obtained are likewise shown in Table 3.

TABLE 3

Performance characteristics of laser-optical computer disks having novel
(Examples 6 and 7) and conventional (Comparative Experiment V2)
dimensionally stable substrates

| Parameter | Example 6[a] | Example 7[b] | Comp. Experiment V2[c] |
|---|---|---|---|
| Tracking characteristics of the computer disks without recorded data | Very good | Very good | Good |
| Recording sensitivity | 1-2 nJ | 1-2 nJ | 1-2 nJ |
| 1st reading: | | | |
| Read signal[d] | Good | Good | Good |

TABLE 3-continued

Performance characteristics of laser-optical computer disks having novel (Examples 6 and 7) and conventional (Comparative Experiment V2) dimensionally stable substrates

| Parameter | Example 6[a] | Example 7[b] | Comp. Experiment V2[c] |
|---|---|---|---|
| Signal-to-noise ratio (dB) | 46 | 45 | 46 |
| Uncorrected bit error rate | $<10^{-5}$ | $<10^{-5}$ | $10^{-5}$ |
| Tracking characteristics | Very good | Good | Unsatisfactory |
| 2nd reading | | | |
| Read signal[d] | Good | Good to satisfactory | Satisfactory |
| Signal-to-noise ratio (dB) | 45 | 43 | 32 |
| Uncorrected bit error rate | $<10^{-5}$ | $<10^{-5}$ | $>10^{-5}$ |
| Tracking characteristics | Very good | Good | Unsatisfactory |

[a] Dimensionally stable substrate from Example 4
[b] Dimensionally stable substrate from Example 5
[c] Dimensionally stable substrate from Comparative Experiment V1
[d] The criterion is both the height (intensity) and the width of the read signal generated by a thermally altered area (bit); determined using an oscilloscope; rating: good (well defined strong signals); satisfactory (somewhat broadened strong signals); unsatisfactory (very broad and/or weak signals)

The results may be summarized as follows:

While the performance characteristics determined largely by the dye layer itself, such as recording sensitivity and read signal, were influenced only slightly, if at all, by the different dimensionally stable substrates, in the laser-optical computer disks having the novel substrates (Examples 6 and 7) the signal-to-noise ratio, the uncorrected bit error rate and in particular the tracking showed a substantial improvement over the prior art in the first reading: those parts of the laser-optical computer disks having the known substrates on which data had been recorded could scarcely be read, whereas in the case of the laser-optical computer disks having the novel substrates tracking could easily be maintained, and here too the recorded information could therefore be recovered virtually without error.

The results obtained in the second reading of the laser-optical computer disks show clearly the extent to which the performance characteristics of the dimensionally stable substrates used are determined by their composition: for example, the laser-optical computer disks having novel substrates still have good or very good performance characteristics after prolonged storage in daylight, whereas the laser-optical computer disks having the known substrates exhibit considerable defects, further underlining the particularly advantageous properties of the novel dimensionally stable substrates.

We claim:

1. An optically transparent, isotropic molding for optical purposes which is free of orientation birefringence, consisting of a mixture consisting essentially of polyphenylene ethers, vinylaromatic polymers and from 1 to 1,000 ppm, based on its total amount, of one or more additives selected from the group consisting of the compounds of the formula I

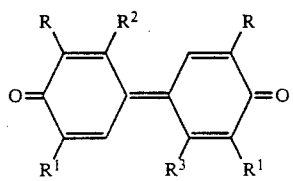

and of the formula II

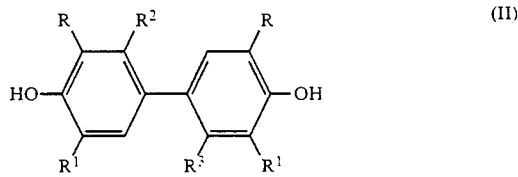

where R and $R^1$ may be identical or different and are each hydrogen, chlorine, bromine, substituted or unsubstituted $C_1$-$C_6$-alkyl, $C_3$-$C_6$-alkenyl, substituted or unsubstituted $C_5$-$C_{18}$-aryl or $C_1$-$C_6$-alkoxy, and a) the radicals R are each hydrogen or methyl if the radicals $R^1$ are each chlorine or bromine, b) the radicals R are each methyl if the radicals $R^1$ are each isopropyl and c) tert-butyl group is excepted, and $R^2$ and $R^3$ are each hydrogen, hydroxyl or $N(R^4)_2$, and d) $R^3$ is hydrogen only when $R^2$ is hydroxyl or $N(R^4)_2$, e) $R^3$ is $N(R^4)_2$ only when $R^2$ has the same meaning, and f) the two radicals $R^1$ on one nitrogen atom may be identical or different and are each branched, straight-chain or cyclic alkyl or branched, straight-chain or cyclic aza- or oxaalkyl, or the two radicals $R^4$ are bonded cyclically to one another via a divalent group.

2. A molding for optical purposes as claimed in claim 1, wherein the mixture contains from 10 to 10,000 ppm, based on its total amount, of oligomeric polyphenylene ethers of the formula VI

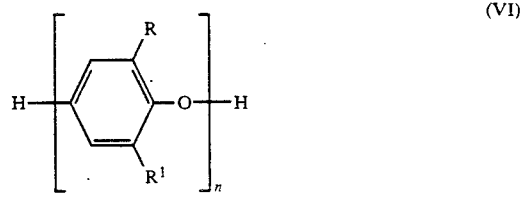

where R and $R^1$ have the meanings stated in claim 1 and n is an integer of from 3 to 15.

3. A molding for optical purposes as claimed in claim 1, wherein R and $R^1$ are each methyl 4. A molding for optical purposes as claimed in claim 1, wherein $R^4$ is n-butyl.

5. A molding for optical purposes as claimed in claim 1, wherein the mixture is opaque to light of wavelength $\lambda < 400$ nm and transparent to light of wavelength $\lambda > 400$ nm.

6. A molding for optical purposes as claimed in claim 1, wherein the mixture has an intrinsic viscosity $[\eta]$ of from 0.5 to 0.8, measured in 0.5% strength solution in chloroform at 25° C.

7. A molding for optical purposes as claimed in claim 1, wherein the polyphenylene ethers and the vinylaromatic polymers are present in the mixture in a weight ratio of from 30 : 70 to 50 : 50.

8. A molding for optical purposes as claimed in claim 7, wherein the polyphenylene ethers and the vinylaromatic polymers are present in the mixture in a weight ratio of from 35 : 65 to 40 : 60.

9. A molding for optical purposes as claimed in claim 1, wherein the polyphenylene ethers have an intrinsic viscosity $[\eta]$ of from 0.5 to 0.6, measured in 0.5% strength solution in chloroform at 25° C.

10. A molding for optical purposes as claimed in claim 1, wherein the polyphenylene ethers have a nonuniformity of molecular weight $\overline{M}_w/\overline{M}_n$ of from 4 to 11.

11. A molding for optical purposes as claimed in claim 10, wherein the polyphenylene ethers have a number average molecular weight $\overline{M}_n$ of from 3,500 to 7,000.

12. A molding for optical purposes as claimed in claim 10, wherein the polyphenylene ethers have a weight average molecular weight $\overline{M}_w$ of from 30,000 to 50,000.

13. A molding for optical purposes as claimed in claim 11, wherein the polyphenylene ethers have a weight average molecular weight $\overline{M}_w$ of from 30,000 to 50,000.

14. A molding for optical purposes as claimed in claim 1, wherein the polyphenylene ether is poly-(2,6-dimethylphen-1,4-ylene ether).

* * * * *

UNITED STATES PATENT AND TRADEMARK OFFICE
CERTIFICATE OF CORRECTION

PATENT NO. : 5,130,356

DATED : July 14, 1992

INVENTOR(S) : Karl-Heinz FEUERHERD et al.

It is certified that error appears in the above-identified patent and that said Letters Patent is hereby corrected as shown below:

Claim 1, column 30, line 34: "$C_5-C_{18}$-aryl" should read -- $C_6-C_{18}$-aryl --

Claim 1, column 30, line 45: "$R^1$" should read -- $R^4$ --

Signed and Sealed this

Thirty-first Day of August, 1993

*Attest:*

BRUCE LEHMAN

*Attesting Officer*  *Commissioner of Patents and Trademarks*